US007799342B2

(12) United States Patent  (10) Patent No.: US 7,799,342 B2
Szamosi et al. (45) Date of Patent: Sep. 21, 2010

(54) FAST DISSOLVING TABLET

(75) Inventors: Janos Szamosi, Chesterfield, VA (US); Kevin S. Kinter, Glen Allen, VA (US); Vincent H. Li, Mechanicsville, VA (US); Khawla Abdullah Abu-Izza, Wayne, NJ (US)

(73) Assignee: Wyeth LLC, Madison, NJ (US)

( * ) Notice: Subject to any disclaimer, the term of this patent is extended or adjusted under 35 U.S.C. 154(b) by 1055 days.

(21) Appl. No.: 10/643,623

(22) Filed: Aug. 19, 2003

(65) Prior Publication Data

US 2004/0037878 A1 Feb. 26, 2004

Related U.S. Application Data

(63) Continuation-in-part of application No. 09/731,479, filed on Dec. 6, 2000, now Pat. No. 6,733,781.

(51) Int. Cl.
*A61K 9/20* (2006.01)
*A61K 9/46* (2006.01)

(52) U.S. Cl. .................... 424/464; 424/465; 424/466

(58) Field of Classification Search ................ 424/464, 424/465, 466
See application file for complete search history.

(56) References Cited

U.S. PATENT DOCUMENTS

| 4,704,269 | A | * | 11/1987 | Korab |
| 5,178,878 | A | * | 1/1993 | Wehling et al. |
| 5,223,264 | A |   | 6/1993 | Wehling et al. |
| 5,298,261 | A |   | 3/1994 | Pebley et al. |
| 5,401,513 | A |   | 3/1995 | Wehling et al. |
| 5,464,632 | A |   | 11/1995 | Cousin et al. |
| 5,501,861 | A | * | 3/1996 | Makino et al. |
| 5,503,846 | A |   | 4/1996 | Wehling et al. |
| 5,576,014 | A | * | 11/1996 | Mizumoto et al. |
| 5,609,883 | A |   | 3/1997 | Valentine et al. |
| 5,728,403 | A | * | 3/1998 | Mauger et al. |
| 5,762,961 | A |   | 6/1998 | Roser et al. |
| 5,807,577 | A |   | 9/1998 | Ouali |
| 5,807,578 | A |   | 9/1998 | Acosta-Cuello et al. |
| 5,837,285 | A |   | 11/1998 | Nakamichi et al. |

(Continued)

FOREIGN PATENT DOCUMENTS

EP 0345528 B1 12/1992

(Continued)

OTHER PUBLICATIONS

Grunhagen, H. and Muller, O., "Melt Extrusion Technology," Pharmaceutical Manufacturing International, pp. 165-170, 1995.

(Continued)

*Primary Examiner*—Humera N Sheikh
(74) *Attorney, Agent, or Firm*—Stephen E. Johnson; Jeffrey M. Gold

(57) ABSTRACT

The present invention relates to processes for the preparation of tablets which dissolve rapidly in the mouth and provide an excellent mouthfeel. The tablets of the invention comprise a compound which melts at about 37° C. or lower, have a low hardness, high stability and generally comprise few insoluble disintegrants which may cause a gritty or chalky sensation in the mouth. Convenient and economically feasible processes by which the tablets of the invention may be produced are also provided.

2 Claims, 9 Drawing Sheets

Tablet Hardness as a Function of Compression Force

♦ Melt Granulation  ■ Direct Compression

U.S. PATENT DOCUMENTS

| | | | |
|---|---|---|---|
| 5,837,292 A | 11/1998 | Dijkgraaf et al. | |
| 5,853,758 A | 12/1998 | Lo | |
| 5,939,091 A | 8/1999 | Eoga et al. | |
| 6,024,981 A | 2/2000 | Khankari et al. | |
| 6,106,861 A | 8/2000 | Chauveau et al. | |
| 6,200,604 B1 | 3/2001 | Pather et al. | |
| 6,221,392 B1 | 4/2001 | Khankari et al. | |
| 6,280,770 B1 | 8/2001 | Pather et al. | |
| 6,299,904 B1 * | 10/2001 | Shimizu et al. | 424/464 |
| 6,365,182 B1 | 4/2002 | Khankari et al. | |
| 6,368,625 B1 | 4/2002 | Siebert et al. | |
| 6,509,036 B2 | 1/2003 | Pather et al. | |
| 2003/0091629 A1 | 5/2003 | Pather et al. | |

FOREIGN PATENT DOCUMENTS

| | | |
|---|---|---|
| EP | 0345628 | 5/1993 |
| EP | 0553777 A2 | 8/1993 |
| EP | 0922464 | 6/1999 |
| EP | 0922464 A1 | 6/1999 |
| JP | 11-35451 | 2/1999 |
| WO | WO 91/04757 | 4/1991 |
| WO | WO 97/38679 | 4/1997 |
| WO | WO 97/18796 | 5/1997 |
| WO | 97/38679 | 10/1997 |
| WO | 98/52541 | 5/1998 |
| WO | WO 98/46215 | 10/1998 |
| WO | 99/44580 | 3/1999 |

OTHER PUBLICATIONS

Aveka Group, http://www.thomasregister.com/olc/aveka/prilling.htm, (May 10, 2000) "Prilling".

Maejima et al., "Preparation of Spherical Beads Without any Use of Solvents by a Novel Tumbling Melt Granulation (TMG) Method," Chem. Pharm. Bull. 45(3), pp. 518-524, 1997.

Schaefer et al., "Drug Development and Industrial Pharmacy," 16(8), pp. 1249-1277, 1990.

Volnovich et al., "Screening of High Shear Mixer Melt Granulation Process Variables Using an Asymmetrical Factorial Design," International Journal of Pharmaceutics, 190, pp. 73-81, 1999.

Brietenbach, Jorg., "Melt Extrusion: An Innovative Technology for Tablet Manufacture," Pharm. Tech. Europe Conf, 13, pp. 8-18, 1998.

Buckton, Graham et al., "The Use of Isothermal Microcalorimetry in the Study of Changes in Crystallinity of Spray-Dried Salbutamol Sulphate," Intl. Journal of Pharmaceutics, 116, pp. 113-118, 1995.

* cited by examiner

Fig. 1: Tablet Hardness as a Function of Compression Force

Fig. 4: Disintegration Time (T2) as a Function of Compression Force

FAST DISSOLVING TABLET

This application is a Continuation in Part of U.S. patent application Ser. No. 09/731,479 filed Dec. 6, 2000 now U.S. Pat. No. 6,733,781, entitled "Fast Dissolving Tablet," the contents of which are incorporated herein in their entirety to the extent that it is consistent with this invention and application.

BACKGROUND OF THE INVENTION

1. Field of the Invention

The current invention relates to tablets of low hardness but good physical stability, in particular fast dissolving tablets that can be made at very low compression force, yet have acceptable stability, and methods for preparing such tablets.

2. Description of the Related Art

Several processes are presently available by which a tablet, which dissolves quickly in the mouth, may be formulated. However, various disadvantages are associated with these currently available methods for producing fast dissolving tablets. For example the addition of high levels of disintegrants is disclosed by Cousin et al. (U.S. Pat. No. 5,464,632). Cousin et al. add two disintegrants to the disclosed tablet formulations, for example 16% starch 1500 and 13.3% crossprovidone. The oral-disintegration time of these tablets is 35 seconds to 45 seconds. However, tablets including high levels of disintegrants have a chalky or dry feel when placed in the mouth.

Another process for producing fast dissolving tablets involves freeze drying or lyophilizing solutions or suspensions of an active ingredient and matrix forming excipients. Pebley et al. (U.S. Pat. No. 5,298,261) disclose freeze-drying a slurry or paste comprising an active ingredient and excipients placed in blister packets. Humbert-Droz et al. (WO 97/36879) disclose vacuum drying, at room temperature or a slightly elevated temperature, a suspension including the active drug, a sugar alcohol, PEG 6000, talc, sweeteners and flavors in preformed blisters. The disadvantages of the freeze drying or vacuum drying methods are time (very slow process), cost of the equipment (not done on conventional tablet manufacturing equipment), and that it is limited to low dose actives.

Fast-dissolving tablets may also be formulated by the inclusion of effervescent coupled compounds. Wehling et al. (U.S. Pat. No. 5,178,878 and WO 91/04757) disclose the addition of an effervescent couple (such as sodium bicarbonate and citric acid) to a tablet. Exposure of the tablet to moisture results in contact and chemical reaction between the effervescent couple which leads to gas production and tablet disintegration. For this reason, tablets which include effervescent pairs are highly sensitive to moisture and have an unpleasant mouthfeel.

Tablets formed by compression under low compression force also dissolve more rapidly than tablets formed by high compression force. However, tablets produced by these processes have a high degree of friability. Crumbling and breakage of tablets prior to ingestion may lead to uncertainty as to the dosage of active ingredient per tablet. Furthermore, high friability also causes tablet breakage leading to waste during factory handling.

The present invention addresses these and other problems associated with the prior art. The invention provides fast-dissolving tablets of low hardness, low friability and high stability which have the added advantage of cost-effective methods of manufacture and are amenable to established manufacturing and packaging methods. In particular, the fast-dissolving tablets of the invention melt rapidly in the mouth and provide an excellent mouth feel.

SUMMARY OF THE INVENTION

The present invention advantageously provides compositions and methods for preparing a fast dissolving tablet of low hardness but good physical stability that can be made at very low compression force.

Thus, the invention provides a tablet comprising a low melting point compound that melts or softens at or below 37° C., a water soluble excipient, and an active ingredient. Preferably, the low melting point compound comprises from about 0.01% to about 20% (wt/wt) of the composition (e.g., 0.01, 0.1, 1, 2.5, 5, 7.5, 10, 12, 14, 16, 18, or 20% (wt/w). Preferably, the tablet has a hardness of about 3 kP or less, more preferably about 2 kP or less, and still more preferably about 1 kP or less. Preferably, the minimum hardness of the tablet is about 0.1 kP, although lower values, including 0.05 kP, are possible. When established manufacturing and packaging methods are used the low melting point compound preferably comprises about 0.01% to about 2% (wt/wt) of the composition and the tablet hardness is preferably about 1.0 to about 2.0 kP and more preferably between about 1.2 and about 1.5 kP.

The invention further provides a method of producing a tablet composition. The method comprises combining an active agent (also termed "active ingredient" or "active") with a fast dissolving granulation. The fast dissolving granulation comprises a low melting point compound and a water soluble excipient. Preferably, the low melting point compound is present in an amount that will yield values (i.e., content thereof) of about 0.01% to about 20% (wt/wt) in a final tablet composition (e.g., 0.01, 0.1, 1, 2, 2.5, 5, 7.5, 10, 12, 14, 16, 18, or 20% (wt/wt)).

The accompanying Detailed Description, Examples and Drawings further elaborate the invention and its advantages.

DETAILED DESCRIPTION OF PREFERRED EMBODIMENTS

Figure 1:
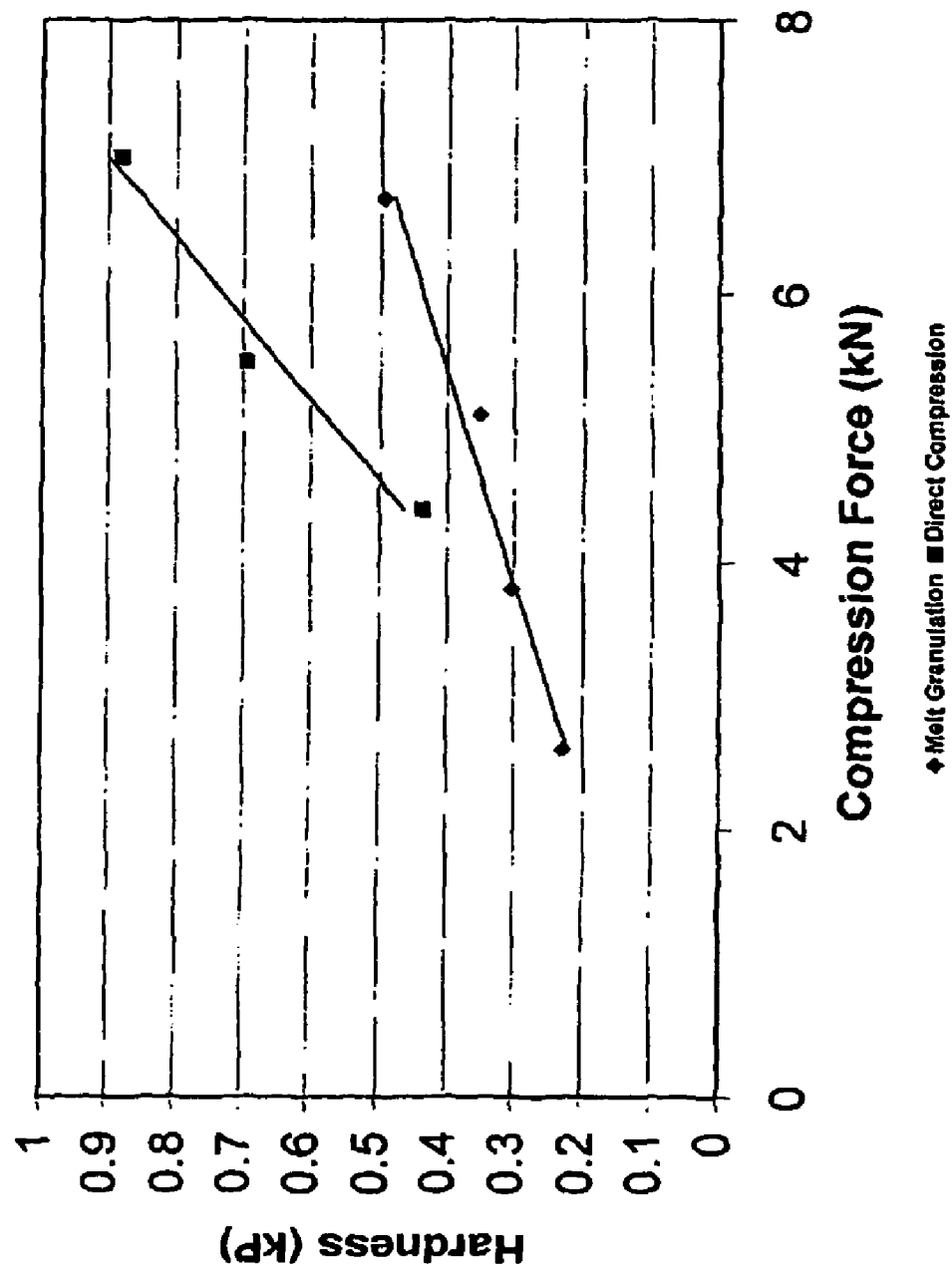
FIG. 1 shows a graph of tablet hardness as a function of compression force for tablets of the invention prepared by a melt granulation process (diamonds), and tablets prepared by direct compression (squares).

The current invention provides fast dissolving tablet formulations that can be formed by compression into a conventional tablet. Tablet friability is lower than conventional fast dissolving tablets prepared by low compression. The fast dissolving tablet has at least one compound (or "component") which partially or fully melts or softens at or below body temperature and a water soluble excipient. Surprisingly, it has been found that use of the component which partially or fully melts below body temperature in an amount of about 0.01% to about 2.5% wt. in the tablet provides for a fast dissolving tablet composition that is conveniently amenable to established tablet manufacturing processes and equipment and to established packaging methods. Amenable to established tablet and manufacturing processes and equipment is taken to mean that the composition (which forms the tablet) may be processed with conventional manufacturing equipment with minimal occurrence of malformed product and/or the need for special equipment maintenance procedures The low melting point compound may be hydrophilic or hydrophobic. The tablets of the invention may also include an active ingredient and may also include one or more disintegrants, flavors, colorants, sweeteners, souring agents, glidants or lubricants.

The hardness of the tablets is low (less than or equal to about 3 kP), preferably less than or equal to about 2 kP, and more preferably less than or equal to about 1 kP, with a minimum hardness of about 0.1 kP (e.g., 0.05, 0.07, 0.1, 0.2, 0.3, 0.4, 0.5, 0.6, 0.7, 0.8, 0.9, 1.0, 1.3, 1.6, 1.9, 2.0, 2.1, 2.3, 2.5, 2.7, 2.8, or 3.0 kP). In embodiments well suited to established manufacturing and packaging methods, the tablet hardness is preferably about 1.2 to about 1.5 kP. In other embodiments, hardness ranges from about 0.2 to about 1 kP. Attributes such as (1) fast stable dissolution; (2) good tablet mouth feel; and (3) good tablet physical stability are of greater importance than minimum and maximum values of tablet hardness. Nevertheless, the tablets are somewhat pliable, and are less fragile than conventional tablets that have the same crushing strength. The tablets have an excellent mouthfeel resulting from the low melting point component which melts or softens in the mouth to produce a smooth feel and masks the grittiness of insoluble ingredients. Unlike other fast dissolving tablets, the disintegration of this fast dissolving tablet occurs by a combination of melting, disintegration of the tablet matrix, and dissolution of water soluble excipient. Therefore, a dry feels does not occur. Disintegration time is 10 to 30 seconds (e.g., 10, 12, 14, 16, 18, 20, 22, 24, 26, 28 or 30 seconds), depending on the tablet size and amount of insoluble ingredients, e.g., coated active. Even though the tablet contains a low melting point ingredient, it is relatively stable to high temperatures. Heating the tablet above the melting point of its low melting point component will not significantly reduce its physical stability.

The friability of conventional tablets is measured by the percentage weight loss after a typical friability test (rotating 10 tablets in a friability apparatus for 100 rotations). This test is very harsh for conventional fast dissolving tablets and so cannot be used to measure their friability. Fast dissolving tablets made by a prior art method of direct compression at low force crumble after a few rotations in the friability apparatus. Fast dissolving tablets manufactured by the method in the current invention can withstand 20-50 rotations in the friability apparatus before any tablet breaks. After 20 rotations, the friability (% weight lost) is typically less than 1%.

The term "low melting point compound" may include any edible compound which melts or softens at or below 37° C. which is suitable for inclusion in the tablets of the invention. Materials commonly used for manufacturing suppositories usually have a melting point at or just below body temperature and can be used in the invention. The low melting point compound can be hydrophilic or hydrophobic.

Examples of hydrophilic low-melting point compounds include, but are not limited to, polyethylene glycol; the preferred mean molecular weight range of polyethylene glycol for use in the tablets of the invention is from about 900 to about 1000. Mixtures of polyethylene glycol with different molecular weights (200, 300, 400, 550, 600, 1450, 3350, 8000 or 10,000) are within the scope of the invention if the mixture melts or softens at or below 37 degrees celsius.

Examples of hydrophobic low-melting point compounds include, but are not limited to, low melting point triglycerides, monoglycerides and diglycerides, semisynthetic glyceride (e.g., EUTECOL®, GELUCIRE® (gatteffosse)), hydrogenated oils, hydrogenated oil derivatives or partially hydrogenated oils (e.g., partially hydrogenated palm kernel oil and partially hydrogenated cottonseed oil), fatty acid esters such as myistyl lactate, stearic acid and palmitic acid esters, cocoa butter or its artificial substitutes, palm oil/palm oil butter, and waxes or mixtures of waxes, which melt at 37° C. or below. In preferred embodiments, the hydrogenated oil is Wecobee M. To be effective in the tablet compositions, the low melting point compound must be edible.

Mono-di-and triglycerides are rarely used as pure components. Hydrogenated vegetable oils and solid or semisolid fats are usually mixtures of mono-di and triglycerides. The melting point of the fat or hydrogenated vegetable oil is characteristic of the mixture and not due to a single component. Witepsol (brand name by Condea), Supocire (brand name by Gattefosse), and Novata (brand name by Henkel) are commonly used in manufacturing suppositories, because they melt at body temperature. All are mixtures of triglycerides, monoglycerides and diglycerides.

In preferred embodiments, the low melting point compound comprises from about 0.01% to about 20%, by weight, of a tablet composition (e.g., about 0.01, 0.1, 1, 2.5, 5, 7.5, 10, 12, 14, 15, 16, 18 or 20% (wt/wt)). Concentration of low melting point compound in the amount of about 0.01% to about 2% (wt/wt) of the tablet are preferable when established manufacturing and packaging methods are used. The tablets of the present invention also include a water soluble excipient. As used herein, the term "water soluble excipient" refers to a solid material or mixture of materials that is orally ingestible and readily dissolves in water. Examples of water soluble excipients include but are not limited to saccharides, amino acids, and the like. Saccharides are preferred water soluble excipients. Preferably, the saccharide is a mono-, di- or oligosaccharide. Examples of saccharides which may be added to the tablets of the invention may include sorbitol, glucose, dextrose, fructose, maltose and xylitol (all monosaccharides); sucrose, lactose, glucose, galatose and mannitol (all disaccharides). In a specific embodiment, exemplified below, the saccharide is lactose. Preferably, the saccharide is mannitol. Other suitable saccharides are oligosaccharides. Examples of oligosaccharides are dextrates and maltodextrins. Modified saccharides such as sucralose or other artificial sweeteners such as saccharin or aspartame, for example, may be used. Other water soluble excipients may include amino acids such as alanine, arginine, aspartic acid, asparagine, cysteine, glutamic acid, glutamine, glycine, histidine, isoleucine, leucine, lysine, methionine, phenylalanine, proline, serine, threonine, tryptophan, tyrosine and valine. Glycine and lysine are preferred amino acids.

In preferred embodiments, the water soluble excipient comprises from about 25% to about 97.5%, by weight, of a tablet composition. The preferred range is about 40% to about 80%. For example, tablet compositions comprising about 25, 30, 35, 40, 45, 50, 55, 60, 65, 70, 75, 80, 85, 90, 95 or 97.5%, by weight, of the excipient, e.g. monosaccharide, disaccharide, polysaccharide, modified saccharide, artificial sweetener or mixtures thereof are within the scope of the invention.

As used herein, the term "about" (or "approximately") means a particular value can have a range acceptable to those of skill in the art given the nature of the value and method by which it is determined. In a specific embodiment, the term means within 50% of a given value, preferably within 20%, more preferably within 10%, and more preferably still within 5%.

Active Ingredients

As used herein, the term "active ingredient" or "active agent" refers to one or more compounds that have some pharmacological property. Accordingly, more than one type of active ingredient compound may be added to the tablets of the invention. The tablets of the invention may comprise any active ingredient which may be orally administered to a subject. Tablets including active ingredients in amounts appropriate for the desired pharmacological properties at the dosage administration can be formulated. Any amount of active ingredient that does not significantly affect beneficial tablet features, such as hardness, friability and mouthfeel are within the scope of the invention. Placebo tablets, which lack an "active ingredient" having a known pharmacologic activity, are also within the scope of the invention. An "active ingredient" of a placebo can be the water soluble excipient (i.e., lacking any identifiable "active"), a different water soluble compound, or any non-active compound.

A non-limiting list of acceptable active ingredients may include but is by no means limited to: 1) antipyretic analgesic anti-inflammatory agents such as indomethacin, aspirin, diclofenac sodium, ketoprofen, ibuprofen, mefenamic acid, dexamethasone, dexamethasone sodium sulfate, hydrocortisone, prednisolone, azulene, phenacetin, isopropylantipyrin, acetaminophen, benzydamine hydrochloride, phenylbutazone, flufenamic acid, mefenamic acid, sodium salicylate, choline salicylate, sasapyrine, clofezone or etodolac; 2) anti-ulcer agents such as ranitidine, sulpiride, cetraxate hydrochloride, gefarnate, irsogladine maleate, cimetidine, lanitidine hydrochloride, famotidine, nizatidine or roxatidine acetate hydrochloride; 3) coronary vasodilators such as Nifedipine, isosorbide dinitrate, diltiazem hydrochloride, trapidil, dipyridamole, dilazep dihydrochloride, methyl 2,6-dimethyl-4-(2-nitrophenyl)-5-(2-oxo-1,3,2-dioxaphosphorinan-2-yl)-1,4-dihydropyridine-3-carboxylate, verapamil, nicardipine, nicardipine hydrochloride or verapamil hydrochloride; 4) peripheral vasodialtors such as ifenprodil tartrate, cinepazide maleate, cyclandelate, cinnarizine or pentoxyfyline; 5) oral antibacterial and antifungal agents such as pencillin, ampicillin, amoxicillin, cefalexin, erythromycin ethylsuccinate, bacampicillin hydrochloride, minocycline hydrochloride, chloramphenicol, tetracyline, erythromycin, fluconazole, itraconazole, ketoconazole, miconazole or terbinafine; 6) synthetic antibacterial agents such as nalidixic acid, piromidic acid, pipemidic acid trihydrate, enoxacin, cinoxacin, ofloxacin, norfloxacin, ciprofloxacin hydrochloride, or sulfamethoxazole trimethoprim; 7) antipasmodics such as popantheline bromide, atropine sulfate, oxapium bromide, timepidium bromide, butylscopolamine bromide, rospium chloride, butropium bromide, N-methylscopolamine methylsulfate, or methyloctatropine bromidebutropium bromide; 8) antitussive, anti-asthamitic agents such as theophylline, aminophylline, methlephedrine hydrochloride, procaterol hydrochloride, trimetoquinol hydrochloride, codeine phosphate, sodium cromoglicate, tranilast, dextromethorphane hydrobromide, dimemorfan phosphate, clobutinol hydrochloride, fominoben hydrochloride, benproperine phosphate, tipepidine hibenzate, eprazinone hydrochloride, clofedanol hydrochloride, ephedrine hydrochloride, noscapine, carbetapentane citrate oxeladin tannate, or isoaminile citrate; 9) broncyodilators such as diprophylline, salbutamol sulfate, cloprenaline hydrochloride, formoterol fumarate, orciprenalin sulfate, pirbuterol hydrochloride, hexoprenaline sulfate, bitolterol mesylate, clenbuterol hydrochloride, terbutaline sulfate, mabuterol hydrochloride, fenoterol hydrobromide, or methoxyphenamine hydrochloride; 10) diuretics such as furosemide, acetazolamide, trichlormethiazide, methyclothiazide, hydrochlorothiazide, hydroflumethiazide ethiazide, cyclopenthiazide, spironolactone, triamterene, fluorothiazide, piretanide, metruside, ethacrygnic acid, azosemide, or clofenamide; 11) muscle relaxants such as chlorphensin carbamate, tolperison hydrochloride, eperisone hydrochloride, tizanidine hydrochloride, mephenesin, chlorozoxazone, phenprobamate, methocarbamol, chlormezanone, pridinol mesylate, afloqualone, baclofen, or dantrolene sodium; 12) brain metabolism altering drugs such as meclofenoxate hydrochloride; 13) minor tranquilizers such as oxazolam, diazepam, clotiazepam, medazepam, temazepam, fludiazepam, meprobamate, nitrazepam, or chlordiazepoxide; 14) major tranquilizers such as sulpiride, clocapramine hydrochloride, zotepine, chlorpromazinon, haloperidol; 15) β-blockers such as pindolol, propranolol hydrochloride, carteolol hydrochloride, metoprolol tartrate, labetalol hydrochloride, acebutolol hydrochloride, butethanol hydrochloride, alprenolol hydrochloride, arotinolol hydrochloride, oxprenolol hydrochloride, nadolol, bucumolol hydrochloride, indenolol hydrochloride, timolol maleate, befunolol hydrochloride, or bupranolol hydrochloride; 16) antiarrhythmic agents such as procainamide hydrochloride, disopyramide, ajimaline, quinidine sulfate, aprindine hydrochloride, propafenone hydrochloride, or mexiletine hydrochloride; 17) gout suppressants allopurinol, probenecid, colchine, sulfinpyrazone, benzbromarone, or bucolome; 18) anticoagulants such as ticlopidine hydrochloride, dicumarol, or warfarin potassium; 19) antiepileptic agents such as phenytoin, sodium valproate, metharbital, or carbamazepine; 20) antihistaminics such as chlorpheniramine maleate, cremastin fumarate, mequitazine, alimenazine tartrate, or cycloheptazine hydrochloride; 21) antiemetics such as difenidol hydrochloride, metoclopramide, domperidone, betashistine mesylate, or trimebutine maleate; 22) hypotensives such as dimethylaminoethyl reserpilinate dihydrochloride, rescinnamine, methyldopa, prazosin hydrochloride, bunazosin hydrochloride, clonidine hydrochloride, budralazine, or urapidin; 23) sympathomimetic agents such as dihydroergotamine mesylate, isoproterenol hydrochloride, or etilefrine hydrochloride; 24) expectorants such as bromhexine hydrochloride, carbocysteine, ethyl cysteine hydrochloride, or methyl cysteine hydrochloride; 25) oral antidiabetic agents such as glibenclamide, tolbutamide, or glymidine sodium; 26) circulatory agents such as ubidecarenone or ATP-2Na; 27) iron preparations such as ferrous sulfate or dried ferrous sulfate; 28) vitamins such as vitamin B1, vitamin B2, vitamin B6, vitamin B12, vitamin C, Vitamin A, vitamin D, vitamin E, vitamin K or folic acid; 29) pollakiuria remedies such as flavoxate hydrochloride, oxybutynin hydrochloride, terodiline hydrochloride, or 4-diethylamino-1,1-dimethyl-2-butynyl (I)-α-cyclohexyl-α-phenylglycolate hydrochloride monohydrate; 30) angiotensin-converting enzyme inhibitors such as enalapril maleate, alacepril, or delapril hydrochloride; 31) anti-viral agents such as trisodium phosphonoformate, didanosine, dideoxycytidine, azido-deoxythymidine, didehydro-deoxythymidine, adefovir, dipivoxil, abacavir, amprenavir, delavirdine, efavirenz, indinavir, lamivudine, nelfinavir, nevirapine, ritonavir, saquinavir or stavudine; 32) high potency analgesics such as codeine, dihydrocodeine, hydrocodone, morphine, dilandid, demoral, fentanyl, pentazocine, oxycodone, pentazocine or propoxyphene; 33) anti-histamines such as Brompheniramine maleate; 34) nasal decongestants such as phenylpropanolamine HCl and 35) antacids such as calcium carbonate, calcium hydroxide, magnesium carbonate, magesium hydroxide, potassium carbonate, potassium bicarbonate, sodium carbonate, and sodium bicarbonate. Active ingredients in the foregoing list may also have beneficial pharmaceutical effects in addition to the one mentioned.

Other Tablet Ingredients

The term "tablet" refers to a pharmacological composition in the form of a small, essentially solid pellet of any shape. Tablet shapes may be cylindrical, spherical, rectangular, capsular or irregular. The term "tablet composition" refers to the substances included in a tablet. A "tablet composition constituent" or tablet constituent" refers to a compound or substance which is included in a tablet composition. These can include, but are not limited to, the active and any excipients in addition to the low melting point compound and the water soluble excipient(s). An excipient is any ingredient in the tablet except the active. In addition to the low melting point compound excipients may include, for example, binders, disintegrants, flavorants, colorants, glidants, souring agents and sweeteners.

For purposes of the present application, "binder" refers to one or more ingredients added before or during granulation to form granules and/or promote cohesive compacts during compression. A "binder compound" or "binder constituent" is a compound or substance which is included in the binder. Binders of the present invention include, at least, the low melting point compound.

Additionally, and optionally, other substances commonly used in pharmaceutical formulations can be included such as flavors (e.g., strawberry aroma, raspberry aroma, cherry flavor, magnasweet 135, key lime flavor, grape flavor trusil art 5-11815, fruit extracts and prosweet), flavor enhancers and sweeteners (e.g., aspartame, sodium saccharine, sorbitol, glucose, sucrose), souring agents (e.g. citric acid), dyes or colorants.

The tablet may also contain one or more glidant materials which improve the flow of the powder blend and minimize tablet weight variation. Glidants such as silicone dioxide may be used in the present invention.

Additionally, the tablets of the invention may include lubricants (e.g. magnesium stearate) to facilitate ejection of the finished tablet from dies after compression and to prevent tablets from sticking to punch faces and each other.

Any method of forming a tablet of the invention into a desired shape which preserves the essential features thereof is within the scope of the invention.

Tablet Formation

A preferred method of forming the tablet compositions of the invention includes preparing a fast dissolving granulation by mixing a low-melting point compound, (preferably a hydrogenated oil, partially hydrogenated oil or hydrogenated oil derivative) and a water soluble excipient, (preferably a saccharide or modified saccharide). The term "fast dissolving granulation" refers to a composition of the low melting point compound and the water soluble excipient prepared for use as a granulation in the manufacture of tablets of the invention. A portion of the fast dissolving granulation may then be added to the remaining ingredients. However, methods of forming the tablets of the invention wherein all tablet constituents are combined simultaneously or wherein any combination of tablet constituents are combined separate from the other constituents are within the scope of the invention.

Granulation end point can be determined visually (visual inspection) or by using a load cell that measures power consumption. Tablet manufacturing and granulation routinely employ both techniques.

The tablet compositions of the invention can be formed by melt granulation which is a preferred method. In particular, the melt granulation can be prepared in a high shear mixer (e.g. high sheer granulation process), low shear mixer or fluid bed granulator. An example of high shear mixer is Diosna (this is a brand name by Diosna Dierks & Söhne GmbH). Examples of low shear mixers are various tumbling mixers (e.g., twin shell blenders or V-blender). Examples of fluid bed granulators are Glatt and Aeromatic fluid bed granulators.

There are at least three ways of manufacturing the granulation:

Melting the low melting point ingredient, then combining (e.g., by spraying) it with the water soluble ingredient(s) (including the water soluble excipient) in the granulator and mixing until granules form.

Loading the water soluble excipient in the granulator and spraying the molten low melting point compound on it while mixing.

Combining the two (water soluble component (including the water soluble excipient) and low melting point component) and possibly other ingredients and mixing while heating to a temperature around a higher than the melting point of the low melting point component until the granules form.

After the granulation congeals, it may be milled and/or screened. Examples of mills that can be used are CoMill, Stokes Oscillator (these are brand names). Any mills that are commonly used for milling tablet granulations may be used.

Melt extrusion can be used to form the fast dissolving granulation. An example of an extruder that can be used is Nica (a brand name by Niro-Aeromatic). The low melting point compound and the water soluble saccharide (or other excipient) are mixed and heated in a planetary mixer bowl (low shear mixer) that is usually part of the extruder. The soft mass is then fed to the extrusion chamber and forced through small holes or orifices to shape it into thin rods or cylinders. After the extruded material congeals it can be milled or spheronized using standard equipment. In the spheronization step, the extrudate is dumped onto the spinning plate of the spheronizer and broken up into small cylinders with a length equal to their diameter, then rounded by frictional forces (See, International Journal of Pharmaceutics 1995, 116:131-146, especially p. 136).

Spray congealing or prilling can also be used to form the tablet compositions of the invention. Spray congealing includes atomizing molten droplets of compositions which, may include low melting point compound, low melting point compound and selected tablet ingredients, or the entire tablet composition onto a surface. The surface may be an inert mechanical support, a carrier surface or in embodiments in which the spray contain droplets only part of the tablet components a second portion of the tablet composition. Equipment that can be used for spray congealing includes spray driers (e.g., Nero spray drier) and a fluid bed coater/granulation with top spray (e.g., Glatt fluid bed coater/granulator). In preferred embodiments, a fast-dissolve granulation is formed wherein, preferably a water soluble excipient, more preferably a saccharide, is suspended in a molten low melting point ingredient and spray congealed. After spray congealing, the resulting composition is allowed to cool and congeal. Following congealing of the mixture, it is screened or sieved and mixed with remaining tablet constituents. Spray congealing processes wherein fast-dissolve granulations comprising any combination of low melting point compound and other tablet constituents are melted and spray congealed onto other tablet constituents are within the scope of the present invention. Spray congealing processes wherein all tablet constituents, including the low-melting point compound, are mixed, the low melting point compound is melted and the mixture is spray congealed onto a surface are also within the scope of the invention.

After spray congealing, the mixture may be milled and then combined with other tablet constituents. Following formation of the final tablet composition, the composition may be further processed to form a tablet shape.

Mixing and milling of tablet constituents during the preparation of a tablet composition may be accomplished by any method which causes the composition to become mixed to be essentially homogeneous. In preferred embodiments the mixers are high-shear mixers such as the Diosna, CoMill or V-Blender.

Once tablet compositions are prepared, they may be formed into various shapes. In preferred embodiments, the tablet compositions are pressed into a shape. This process may comprise placing the tablet composition into a form and applying pressure to the composition so as to cause the composition to assume the shape of the surface of the form with which the composition is in contact. In preferred embodiments, the tablet is compressed into the form at a pressure which will not exceed about 10 kN, preferably less than 8 kN. For example, pressing the tablets at less than 1, 1, 1.5, 2, 2.5, 3, 3.5, 4, 4.5, 5, 6, 7, 8, 9 or 10 kN is within the scope of the invention. The tablets of the invention generally have a hardness of about 3 kP or less; preferably the tablets have a hardness of about 2 kP or less and more preferably about 1 kP or less. For compositions subjected to established manufacturing methods hardness of about 1 to about 2.0 is preferred and harness of about 1.2 to about 1.5 is more preferable. In another embodiment, for example, tablets of less than 0.1 kP including tablets of about 0.05, 0.07 kP and tablets of about 0.2, 0.3, 0.4, 0.5, 0.6. 0.7, 0.8, 0.9, 1.0, 1.3, 1.6, 1.9, 2.0, 2.1, 2.3, 2.5, 2.7, 2.8, or 3.0 are within the scope of the invention. Hydraulic presses such as a Carver Press or rotary tablet presses such as the Stokes Versa Press are suitable means by which to compress the tablet compositions of the invention.

Tablets may also be formed by tumbling melt granulation (TMG) essentially as described in Maejima et al. Chemical Pharmacology Bulletin (1997) 45(3): 518-524; which is incorporated herein by reference. Tumbling melt granulation can be used for preparing the melt granulation. It can be done in a tumbling mixer. The molten low melting point compound is sprayed on the crystalline saccharide and powdered saccharide in the blender and are mixed until granules form. In this case, the low melting point ingredient is the binder and the crystalline saccharide is the seed. An alternative method is to combine the unmelted low melting point ingredient, crystalline sugar (e.g., mannitol or lactose) in the tumbling mixer and mix while heating to the melting point of the low melting point binder or higher. The seed should be crystalline or granular water soluble ingredient (saccharide), e.g., granular mannitol, crystalline maltose, crystalline sucrose, or any other sugar. An example of tumbling mixers is the twin-shell blender (V-blender), or any other shape of tumbling mixers. Heating can be achieved by circulating heated air through the chamber of the granulator and by heating the bottom surface of the chamber. As the seed material and the powdered tablet constitutes circulate the heated chamber, the low-melting point compound melts and adheres to the seeds. The unmelted, powdered material adheres to the seed-bound, molten low-melting point material. The spherical beads which are formed by this process are then cooled and screen sifted to remove nonadhered powdered material.

EXAMPLE 1

Fast Dissolving Granulation

Compositions of Fast Dissolving Granulations. In these compositions, the water soluble excipient is a saccharide. As described above, the tablets of the invention may be formulated by a method wherein a fast dissolving granulation, comprising a low melting point compound and a water soluble excipient, is mixed separately from other tablet constituents. A portion of the fast dissolving granulation may then be combined with the other tablet constituents. In this example, several specific examples of fast dissolving granulations are set forth.

TABLE 1

Fast dissolving granulation formulations.

| Fast Dissolving Granulation Composition | Low Melting Point Compound (amount) | Saccharide (amount) |
|---|---|---|
| 1 | Wecobee M hydrogenated vegetable oil (1 Kg) | mannitol powder (5 Kg) |
| 2 | Gelucire 33/01 semi-synthetic glycerides (200 g) | mannitol powder (1 Kg) |
| 3 | Wecobee M (150 g) | crystalline maltose (100 g) mannitol powder (750 g) |
| 4 | polyethylene glycol 900 (100 g) | fructose powder (400 g) |

Fast dissolving granulations 1 and 2 were prepared by heating the low melting point compound to 50° C. At 50° C., Wecobee M and Gelucire 33/01 become molten. The molten material was gradually added to the mannitol powder in a high shear granulator (Diosna). The granulation was mixed at high speed. When the granulation end point was reached as determined by visual inspection, the granulation was allowed to congeal. The congealed granulation was then milled using a CoMill.

Granulation 3 was granulated by combining melted Wecobee M with the mannitol in a high shear mixer (Robot Coupe) and blending until the granules formed. Granulation 4 was made by combining the melted PEG with fructose powder in a planetary mixer (low shear mixer) and mixing until the granules formed. The granulations were allowed to cool, then were screened.

EXAMPLE 2

Fast Dissolving Ibuprofen Tablets

The following is an example of a fast dissolving tablet wherein the active ingredient is ibuprofen.

| Ingredient | Amount (mg tablet) |
| --- | --- |
| Coated ibuprofen (active ingredient) | 121.9 (equivalent to 100 mg ibuprofen) |
| Citric acid (souring agent) | 11.0 |
| Magnasweet 135 (sweetening agent) | 3.9 |
| Aspartame (sweetening agent) | 6.5 |
| Cherry flavor (flavoring agent) | 7.8 |
| Crosscarmellose sodium (disintegrant) | 39.0 |
| Silicone dioxide (glidant flow aid) | 1.95 |
| Magnesium stearate (lubricant) | 3.25 |
| Fast dissolving granulation 4 | 457.9 |
| Total | 653.2 |

Ingredients were screened, then mixed in a V-blender. Tablets were compressed using a hydraulic press (Carver Press) at 600 lb (about 2.7 kN). The tablets had a hardness of 0.2-0.5 kP and disintegrated in less than 15 seconds.

EXAMPLE 3

Fast Dissolving Antihistamine/Decongestant Tablets

The following is an example of a fast dissolving tablet comprising the active ingredients of many common allergy medications, Phenylpropanolamine HCl and Brompheniramine maleate.

| Ingredient | Amount (mg/tablet) |
| --- | --- |
| Phenylpropanolamine HCI (active ingredient) | 6.25 |
| Brompheniramine maleate (active ingredient) | 1.0 |
| Citric acid (souring agent) | 6.0 |
| Magnasweet 135 (sweetening agent) | 1.80 |
| Aspartame (sweetening agent) | 4.5 |
| Cherry flavor (flavoring agent) | 3.60 |
| Corn Starch (anti-adherent) | 30.0 |
| Silicone dioxide (glidant flow aid) | 3.0 |
| Fast dissolving granulation 4 | 219.25 |
| Magnesium stearate (lubricant) | 2.1 |
| Total | 301.5 |

Tablets were compressed on a hydraulic press (Carver Press) at approximately 3 kN. Tablet hardness was 0.2-0.5 kP and disintegration time 10 seconds.

EXAMPLE 4

Fast Dissolving Ibuprofen Tablets

The following is an example of a fast dissolving tablet wherein the active ingredient is ibuprofen.

| Ingredient | Amount (mg/tablet) |
| --- | --- |
| Coated ibuprofen (active agent) | 119.0 |
| Citric Acid (souring agent) | 20.0 |
| Magnasweet 135 (sweetening agent) | 7.5 |
| Aspartame (sweetening agent) | 7.5 |
| Grape flavor Trusil Art 5-11815 (flavoring agent) | 5.00 |
| Prosweet (flavor and sweetness enhancer) | 5.00 |
| Crosscarmellose sodium (enhancer) | 20.0 |
| Corn Starch, NF (anti-adherent) | 40.0 |
| Silicone dioxide (Syloid 244) (glidant flow aid) | 5.00 |
| Fast dissolving granulation 1 | 271 |
| Total | 500 |

Tablets were compressed using a rotary press (Stokes Versa Press) at 3.3.-3.5 kN, resulting in a hardness of 0.2-0.9 kP. In vivo disintegration time was 19 seconds (average of 34 subjects).

Sensory study: The melt granulation tablets of Example 4 were evaluated for in vivo disintegration time and mouthfeel in an in-house sensory study. The comparator was Kidtab®, an 80 mg acetaminophen fast dissolving tablet prepared by direct compression. Two other ibuprofen fast dissolving tablets prepared by direct compression were also included in the study. The study included 34 subjects. The subjects were asked to record the time for the tablet to completely dissolve in the mouth and give scores for mouthfeel attributes and overall liking of the product. The melt granulation prototype (based on this invention) performed best on disintegration time (FIG. 6) and mouthfeel attributes (least grittiness (FIG. 7) and least chalkiness (FIG. 8)) and were ranked best on the overall performance by the panelists. The following table shows the ranking results of the sensory study on disintegration time and mouthfeel attributes: MG is the melt granulation tablet of the invention. DC1 and DC2 are the two direct compression phototypes.

| | Ranking (1 = best, 4 = worst) Prototype/Product | | | |
| --- | --- | --- | --- | --- |
| Sensory Attribute | DC1 | MG | Kidtab | DC2 |
| Time to dissolve (seconds) | 2 | 1 | 4 | 3 |
| Grittiness | 4 | 1 | 2 | 3 |
| Chalkiness | 3 | 1 | 4 | 2 |
| Overall Preference | 4 | 1 | 2 | 3 |

The tablets of the invention were ranked the highest (1, best) in all four categories tested (dissolution time, grittiness, chalkiness and overall performance) against DC1, DC2 and KIDTAB.

Figure 6:
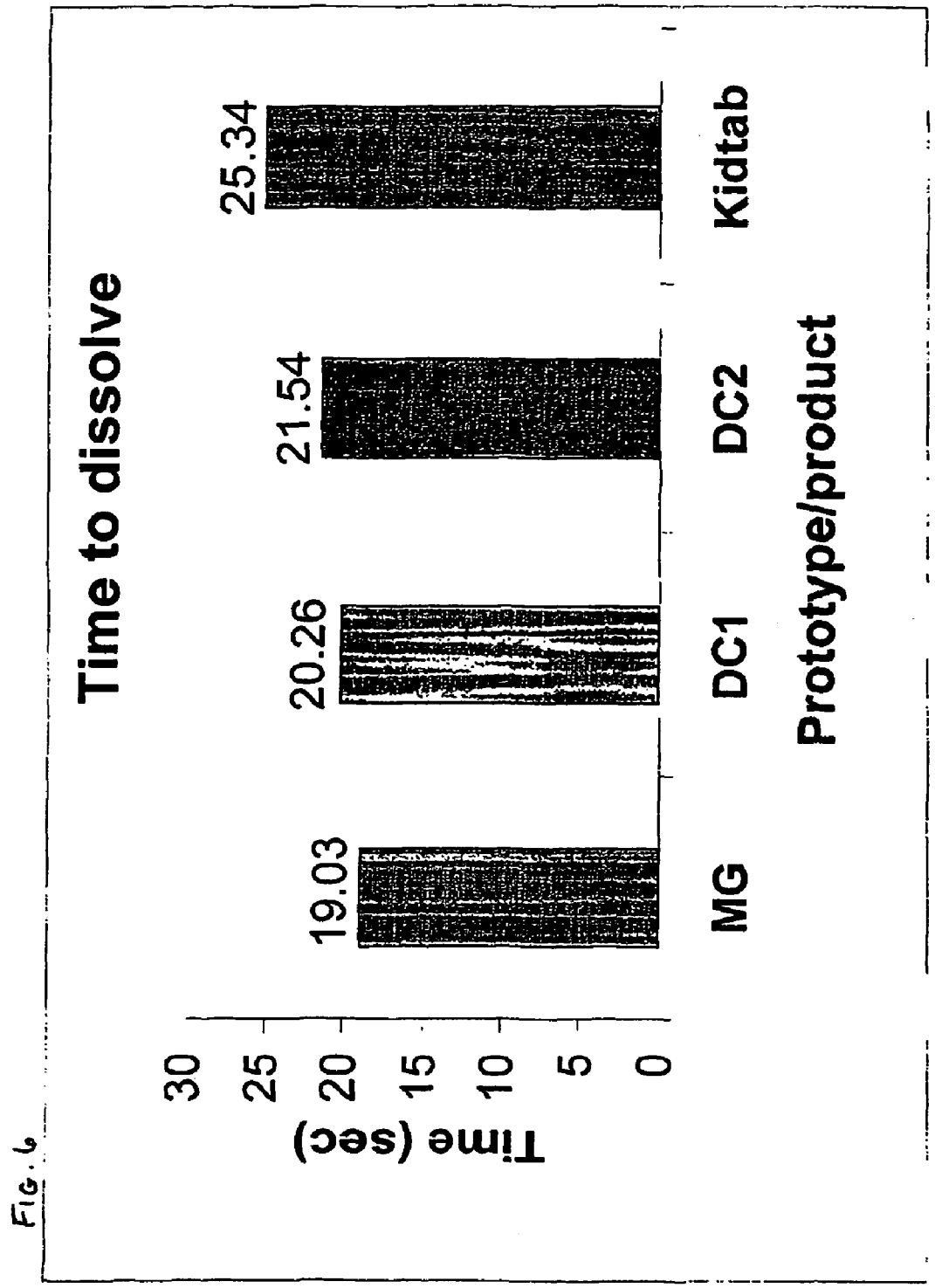
FIG. 6 shows a graph of time to dissolve (mean of disintegration time in seconds for 34 samples of a tablet of the invention (MG), two types of tablets formed by direct compression (DC1 and DC2), and a commercial fast dissolving tablet (KIDTAB®).
Figure 7:
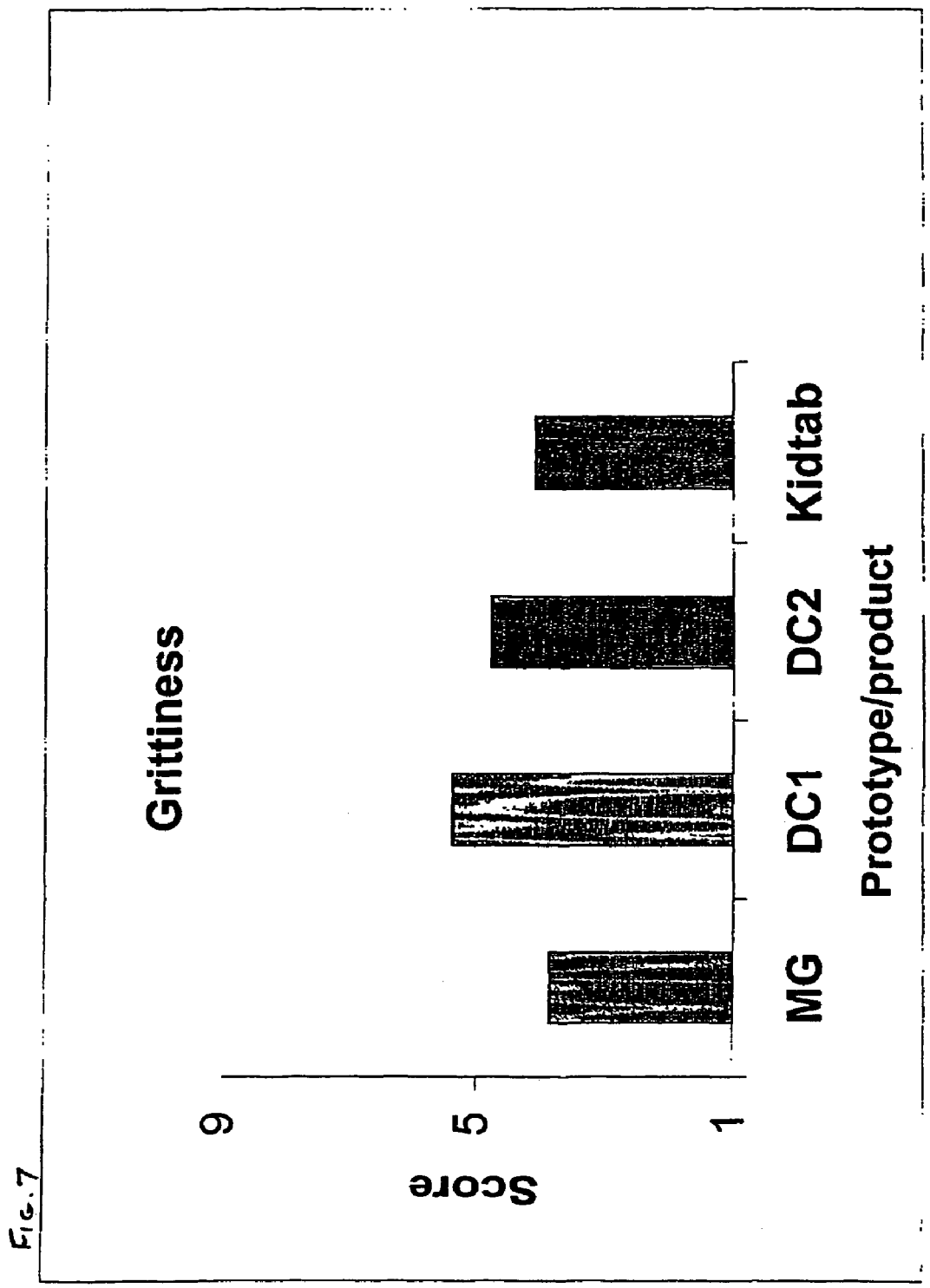
FIG. 7 shows a graph of grittiness score (adjusted mean determined by least squares from ANOVA). Subjects scored this sensory attribute on a scale of 1 (low grittiness) to a 9 (high grittiness). Tablets were as described for FIG. 6.
Figure 8:
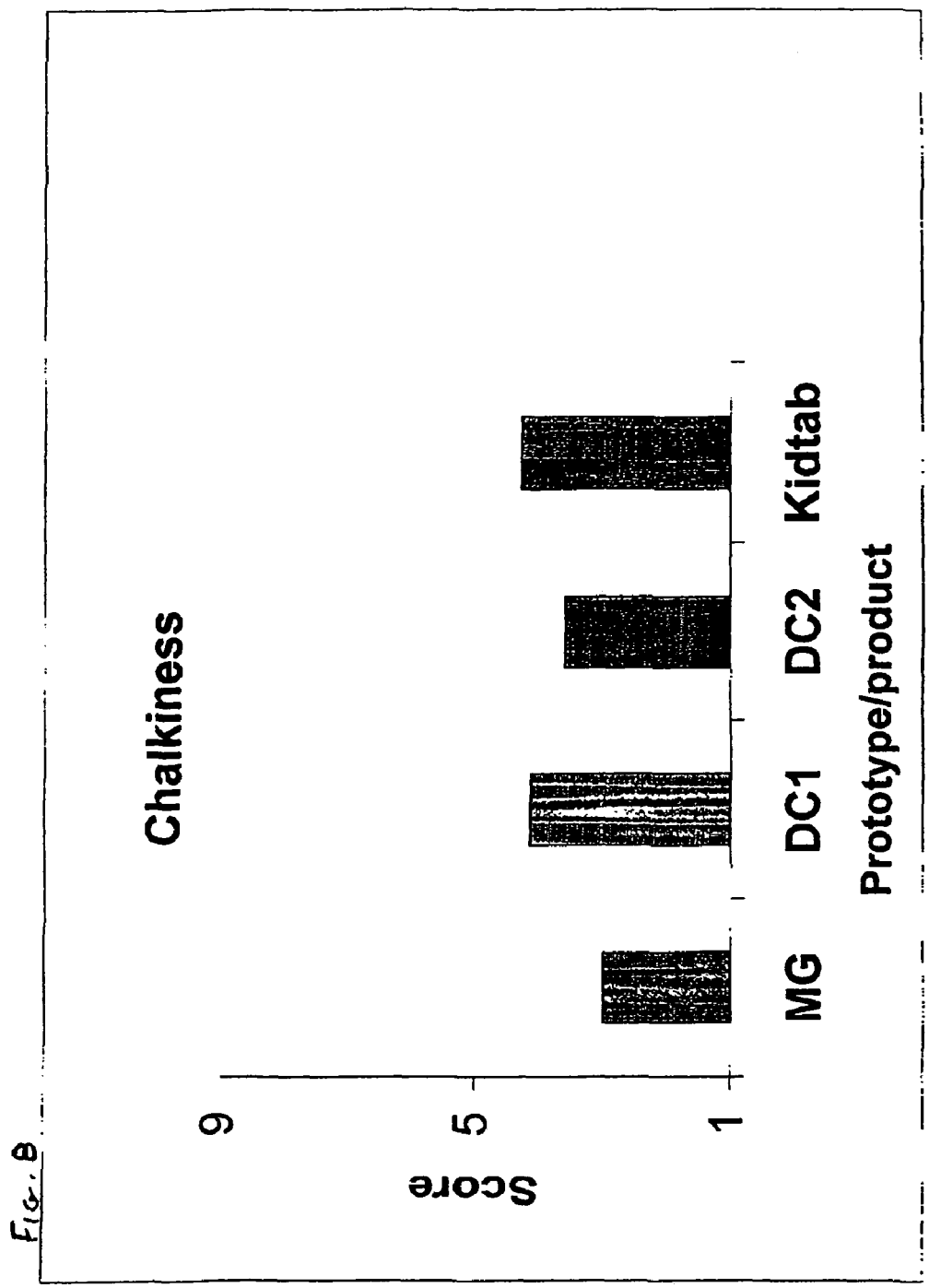
FIG. 8 shows a graph of chalkiness score (adjusted mean determined by least squares from ANOVA). Subjects scored this sensory attribute on a scale of 1 (low chalkiness) to a 9 (high chalkiness). Tablets were described for FIG. 6.

As illustrated in FIG. 6, the tablets of the invention exhibited superior fast dissolving characteristics as compared to the direct compression tablets which were also evaluated (DC1, DC2 and KIDTAB); the average time for the tablet of the invention (MG) to dissolve was 19 seconds wherein the time for DC1, DC2 and KIDTAB to dissolve were about 20, 22 and 25 seconds, respectively. The tablets of the invention also exhibited a mouthfeel which was superior to the DC1, DC2 and KIDTAB tablets. FIGS. 7 and 8 indicate the 34 individuals who participated in the study perceived a lower level of grittiness and chalkiness associated with the tablets of the invention as compared to the direct compression tablets (DC 1, DC2 and KIDTAB).

Figure 9:
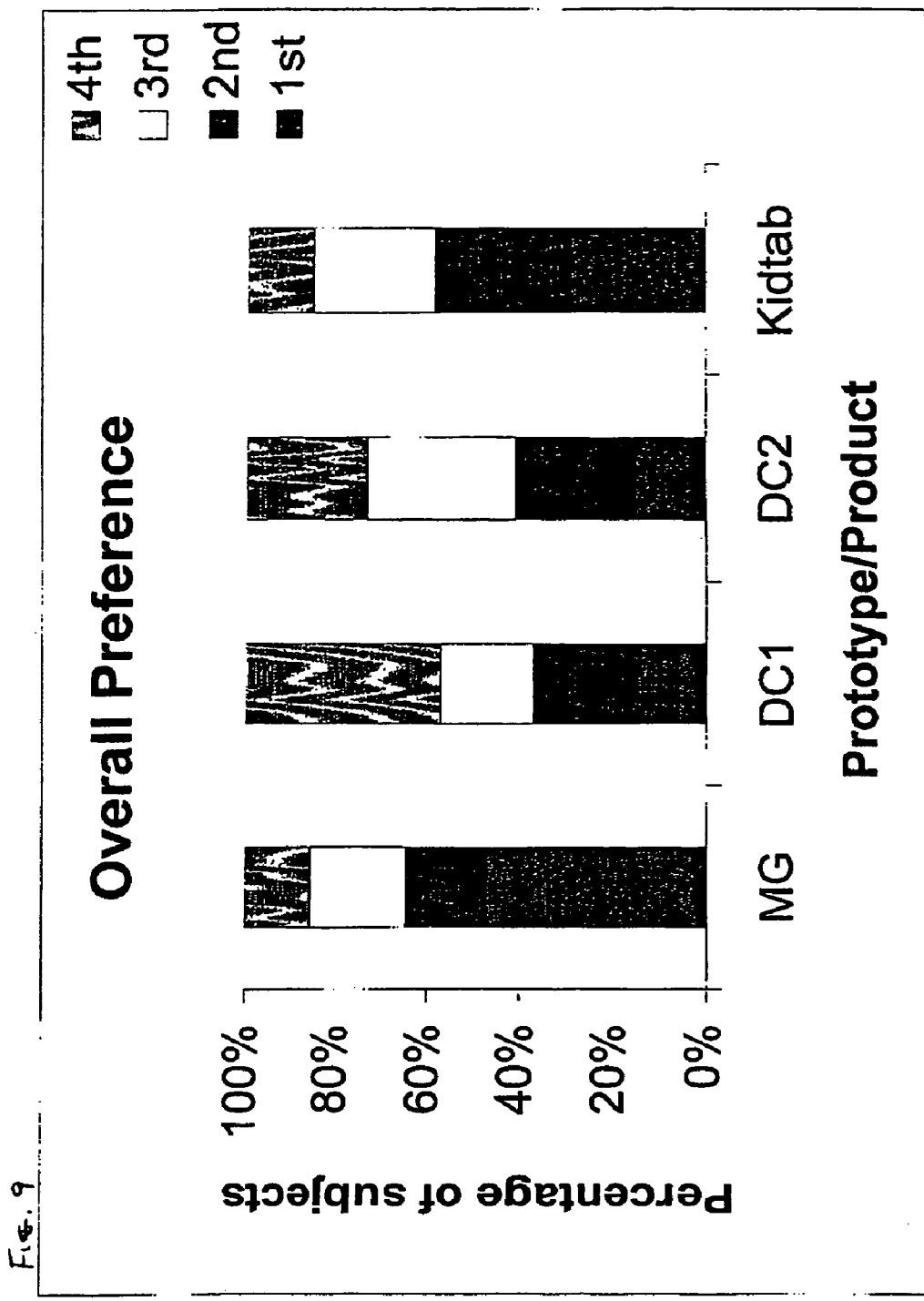
FIG. 9 shows a graph of overall preference ranking for each product (as described in FIG. 6), represented by the percentage of subjects ranking each product $1^{st}$, $2^{nd}$, $3^{rd}$, or $4^{th}$

Overall preference was also scored (least squares mean from ANOVA) on a scale from 1 (most preferred) to 9 (least preferred). As indicated in FIG. 9, the tablet of the invention scored highest (2.11), followed by the KIDTAB® (2.29), and the two direct compression tablets (DC2-2.52, DC1-03.05).

EXAMPLE 5

Fast Dissolving Ibuprofen Tablets

The following is an example of a fast dissolving tablet wherein the active ingredient is ibuprofen.

| Ingredient | (mg/tablet) |
| --- | --- |
| Coated ibuprofen (active agent) | 238.0 |
| Citric Acid (souring agent) | 17.5 |
| Magnasweet 135 (sweetening agent) | 9.75 |
| Aspartame (sweetening agent) | 9.75 |
| Key Lime flavor (flavoring agent) | 6.50 |
| Vanilla powder (flavoring agent) | 0.650 |
| Corn Starch, NF (anti-adherent) | 52.0 |
| Silicone dioxide (Syloid 244) (glidant/flow acid) | 6.50 |
| Sodium stearyl fumarate (Pruv) (lubricant) | 4.88 |
| Fast dissolving granulation 1 | 304 |
| Total | 650 |

Tablets were compressed using a rotary tablet press (Stokes Versa Press) at 3 kN, resulting in a hardness of 0.35-0.60 kP. In vivo disintegration time was 16 seconds.

EXAMPLE 6

Compressibility and In Vitro Evaluation of Tablets

To compare fast dissolving tablets of the invention with fast dissolving tablets prepared by direct compression, the following two examples were prepared.

Melt granulation fast dissolving tablet:

| Ingredient | (mg/tablet) |
| --- | --- |
| Ibuprofen microcaps | 119.0 |
| Citric Acid, anhydrous, fine granular | 20.0 |
| Magnasweet 135 | 7.5 |
| Aspartame (Nutrasweet) | 7.5 |
| Cherry Berry flavor | 4.25 |
| Sweet AM | 2.50 |
| Crosscarmellose sodium | 20.0 |
| Corn Starch, NF | 40.0 |
| Silicone dioxide (Syloid 244) | 5.00 |
| Fast dissolve granulation* | 274.25 |
| TOTAL | 500 |

*The granulation is 85.0% Mannitol powder, USP and 15.0% Wecobee M (hydrogenated vegetable oil). The granulation was prepared similar to granulation 1 in Table 1.

Direct compression fast dissolving tablet.

| Ingredient | mg/tablet |
| --- | --- |
| Ibuprofen microcaps | 119.0 |
| Citric Acid, anhydrous, fine granular | 20.0 |
| Magnasweet 135 | 7.5 |
| Aspartame (Nutrasweet) | 7.5 |
| Sweet AM | 2.5 |
| Fruit Punch flavor | 3.50 |
| Crosscarmellose sodium | 20.0 |
| Corn Starch, NF | 40.0 |
| Silicone dioxide (Syloid 244) | 5.00 |
| Mg Stearate | 3.50 |
| Fast Dissolve granulation | 271.5 |
| TOTAL | 500 |

Melt granulation tablets and direct compression tablets were prepared based on the same formula, except that granular mannitol was used instead of the fast dissolve melt granulation. The compressibility of the two tablet formulations (melt granulation and direct compression) were compared. The two blends were compressed at different compression forces and the resulting tablets were evaluated for hardness and in vitro disintegration time. Tablet hardness (crushing strength) was measured using a high resolution texture analyzer (Stable Microsystems) with an acrylic cylindrical probe.

In vitro disintegration was performed in a texture analyzer. A tablet was held on a net that was then attached to a ¼" stainless steal ball probe. The disintegration medium was 5 ml of water in a 50 ml beaker. The height of water was barely enough to submerge the tablet, and the water temperature was kept at 37±1° C. The texture analyzer was instructed to apply a small force (20 g) when the tablet hit the bottom of the beaker. The time for disintegration onset and total disintegration time was recorded.

Compressibility: Fast dissolving tablets in general are soft and need to be blister-packaged directly off the tablet press. The tablets manufactured according to the invention can be compression or wet granulation. For fast dissolving tablets containing a coated active, it is important to compress at the lowest force possible so that the coating will not be ruptured under compression. With the melt granulation approach, tablets that are robust enough to withstand packaging right off the tablet press were obtained using a compression force as low as 2 kN, whereas for a similar direct compression formulation, acceptable tablets could not be obtained at compression forces below 5 kN (FIG. 1).

Hardness and Friability: Although the melt granulation tablets had a lower hardness compared to direct compression tablets that are compressed at the same force (FIG. 1), the melt granulation tablets were somewhat pliable and less fragile. As illustrated in FIG. 2, the softest melt granulation prototype, with a hardness of about 0.2 kP, was able to withstand at least 9 rotations in the friabilator (friability apparatus) before any tablet breaks. At 0.5 kP, these tablets survived 20-30 rotations. Direct compression tablets at about 0.45 kP started breaking after 4 rotations, while the hardest direct compression prototype with about 0.9 kP hardness only survived 12 rotations. In the same friability test, Kidtab® tablets (marketed fast dissolving tablets prepared by direct compression) started breaking after 5-10 rotations. The average hardness of Kidtab tablets was 1.8 kP. Moreover, at the end of the test, the direct compression tablets showed more chipping around the edges than melt granulation prototypes. Direct compression tablets with hardness greater than 1 kP were not fast dissolving (took 1 minute or more to dissolve in the mouth of a subject).

Figure 3:
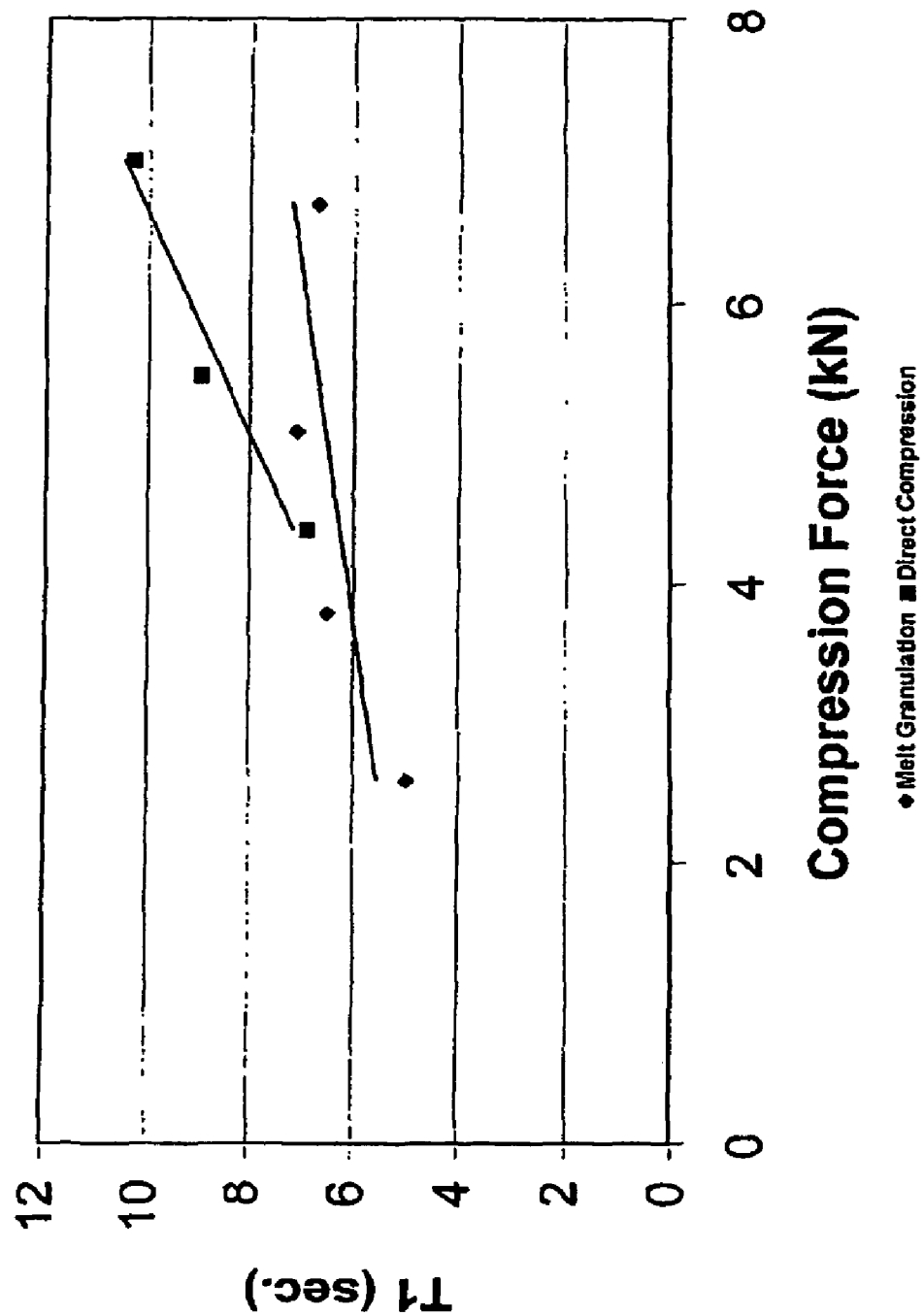
FIG. 3 shows a graph of time onset of disintegration (T1) as a function of compression force for tablets of the invention (diamonds) and for tablets formed by direct compression (squares).
Figure 4:
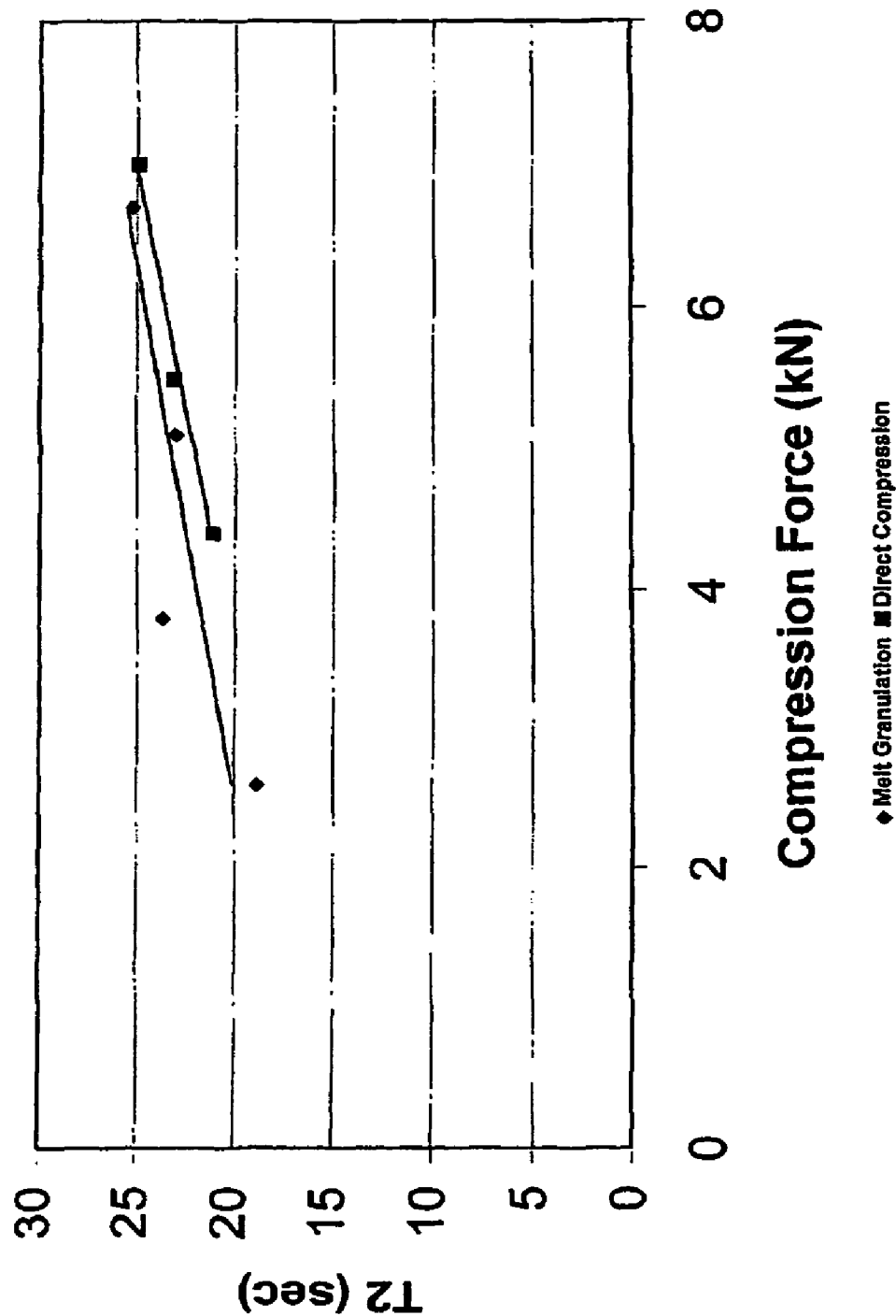
FIG. 4 shows a graph of disintegration time (T2) as a function of compression force for tablets of the invention (diamonds) and for tablets formed by direct compression (squares).
Figure 5:
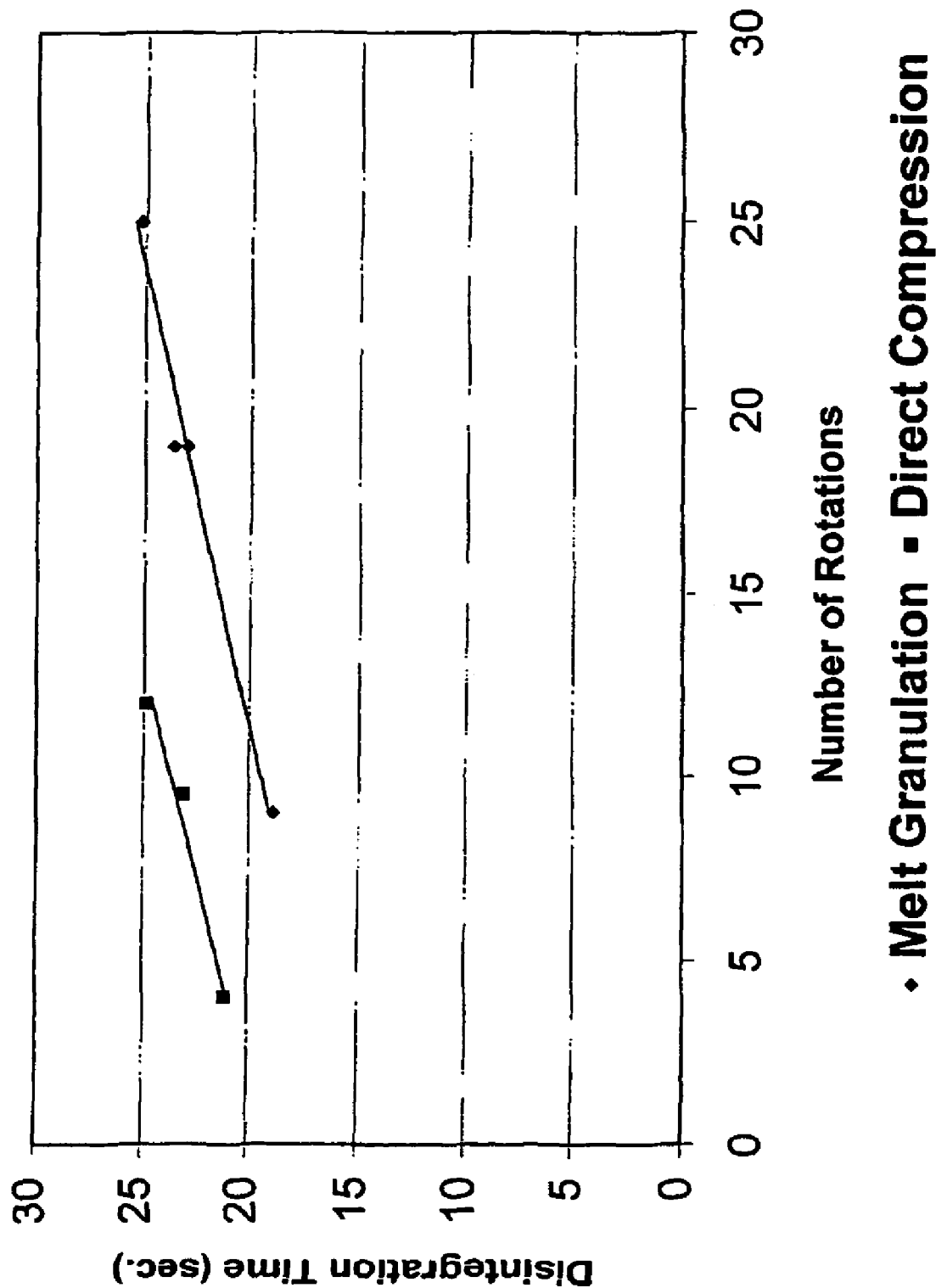
FIG. 5 shows a graph of disintegration time as a function of the friability (as measured by the number of rotations in a Friabilator before a first tablet breaks) for tablets of the invention (diamonds) and for tablets formed by direct compression (squares).

In vitro Disintegration: The onset of disintegration was faster for the melt granulation prototypes compared to direct compression prototypes prepared at the same compression force (FIG. 3). Furthermore, the total time for in vitro disintegration was dependent on compression force regardless of the formulation (FIG. 4). We obtained acceptable tablets from the melt granulation processing low compression force. Direct compression tablets could not be obtained at the same compression force. Therefore, for tablets with similar friability, the melt granulation approach produced faster disintegration time (FIG. 5).

Figure 2:
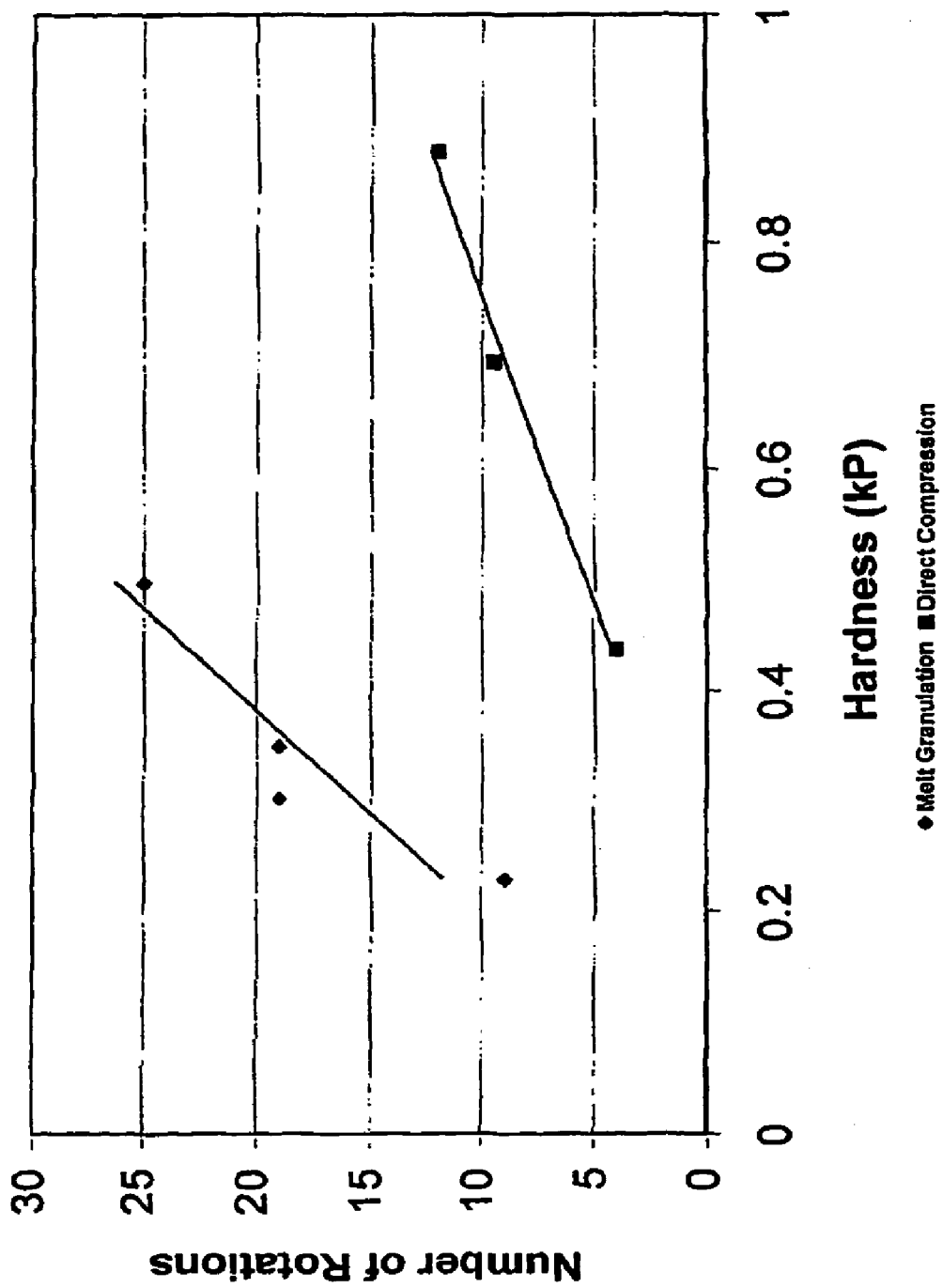
FIG. 2 shows a graph of friability as a function of tablet hardness; "Number of Rotations" indicates a number of rotations in a Friabilator which occur before a tablet breaks. Tablets prepared by melt granulation (diamonds) or by direct compression (squares) were evaluated.

The melt granulation was less sensitive to small changes in compression force, whereas for the direct compression formulation, both hardness and onset of disintegration increased sharply with increasing the compression force (FIGS. 1 and 3).

EXAMPLE 7

Example of Melt Granulation Tablets with Higher Hardness

| Ingredient | mg/tablet |
|---|---|
| Ibuprofen microcaps (encapsulated ibuprofen) | 121.9 |
| Citric Acid, anhydrous, fine granular | 11.0 |
| Magnasweet 135 | 4.0 |
| Aspartame (Nutrasweet) | 6.0 |
| Cherry flavor | 6.0 |
| Sweet AM | 0.5 |
| Crosscarmellose sodium | 45.0 |
| Corn Starch, NF | 40.0 |
| Silicone dioxide (Syloid 244) | 2.50 |
| Fast dissolve granulation | 263.1 |
| TOTAL | 500 |

*The granulation is 85.0% Mannitol powder, USP and 15.0% Wecobee M (hydrogenated vegetable oil).

Tablets were compressed on Stokes Versapress. Compression force was not recorded. Tablet hardness was 1.5 kP. The tablets had a friability of less than 1.0% after 50 rotations in the friabilator, i.e, lost less than 1% of their initial weight and no tablet broke. Mean in vivo disintegration time was 25.8 seconds (12 subjects were asked to take the tablets and record the time it takes for the tablet to completely dissolve without chewing).

EXAMPLE 8

Example of Melt Granulation Tablets Amendable to Established Tablet Manufacturing Process and Packaging Methods

| Ingredient | mg/tablet |
|---|---|
| Composition 1 | |
| Ibuprofen microcaps | 238.0 |
| Sucralose | 5.6 |
| Citric acid | 28.0 |
| Lemon-lime flavor | 1.4 |
| Crosscamellose | 28.0 |
| Mannitol SD200 | 315.0 |
| Corn starch | 42.0 |
| CabOSil | 7.0 |
| Fast Dissolve Granulation* | 35.0 |
| Composition 2 | |
| Ibuprofen microcaps | 238.0 |
| Sucralose | 5.6 |
| Citric acid | 28.0 |
| Lemon-lime flavor | 1.4 |
| Crosscamellose | 28.0 |
| Mannitol SD200 | 280.0 |
| Corn starch | 42.0 |
| CabOSil | 7.0 |
| Fast Dissolve Granulation* | 70.0 |
| Composition 3 | |
| Ibuprofen microcaps | 238.0 |
| Sucralose | 5.6 |
| Citric acid | 28.0 |
| Lemon-lime flavor | 1.4 |
| Crosscamellose | 28.0 |
| Mannitol SD200 | 297.5 |
| Corn starch | 42.0 |
| CabOSil | 7.0 |
| Fast Dissolve Granulation* | 52.5 |

Note:
The Fast Dissolve Granulation* had 17% Wecobee and 83% mannitol powder, so the three formulations had 0.85%, 1.7% and 1.275% Wecobee.
Compositions 1, 2 and 3 were compressed using a rotary press (Stokes Versa Press) to a hardness range of 0.45–1.4 kP for Composition 1, a hardness of 0.7–1.7 kP for composition 2 and a hardness of 1.8 to 2.2 kP for Composition 3.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed:

1. A tablet consisting of a fast dissolve granulation, an active ingredient, mannitol, sucralose, a flavor, a disintegrant, corn starch and silicon dioxide wherein the fast dissolve granulation consists essentially of a portion of the mannitol and a low melting point compound that melts or softens at or below 37° C. selected from the group consisting of hydrogenated vegetable oil, and partially hydrogenated vegetable oil and wherein the low melting point compound comprises less than about 20% (wt/wt) of the fast dissolve granulation and from about 0.01% to about 2.5% (wt/wt) of the tablet, and wherein the tablet has a hardness of less than 1.5 kP and is a fast dissolving tablet.

2. A tablet consisting of a fast dissolve granulation, an active ingredient, mannitol, sucralose, a flavor, a disintegrant, corn starch, silicon dioxide and a souring agent wherein the fast dissolve granulation consists essentially of a portion of the mannitol and a low melting point compound that melts or softens at or below 37° C. selected from the group consisting of hydrogenated vegetable oil, and partially hydrogenated vegetable oil and wherein the low melting point compound comprises less than about 20% (wt/wt) of the fast dissolve granulation and from about 0.01% to about 2.5% (wt/wt) of the tablet, and wherein the tablet has a hardness of less than 1.5 kP and is a fast dissolving tablet.

* * * * *